United States Patent [19]

Gelius et al.

[11] 4,063,807
[45] Dec. 20, 1977

[54] PERIMETRIC EYE TESTING DEVICE

[75] Inventors: Siegfried Gelius; Hanne-Lore Wieczorek; Adolf Triller, all of Munich; Nils Nielsen, Raubling, all of Germany

[73] Assignee: Optische Werke G. Rodenstock, Germany

[21] Appl. No.: 659,787

[22] Filed: Feb. 20, 1976

[30] Foreign Application Priority Data

Feb. 22, 1975   Germany ............................. 2507723
Nov. 25, 1975   Germany ............................. 2552839

[51] Int. Cl.$^2$ ........................... A61B 3/02; A61B 3/04
[52] U.S. Cl. ....................................... 351/24; 351/35; 351/36
[58] Field of Search ....................... 351/23, 24, 30, 35, 351/36

[56]  References Cited
U.S. PATENT DOCUMENTS 3,421,498   1/1969   Gans ................................. 351/24 X
3,837,734   9/1974   Regan ............................... 351/23 X

OTHER PUBLICATIONS

Theodore E. Cohen et al., "The Drodewand ... Perimetry," *Am. J. Optom & Physiol Optics*, vol. 51, No. 12, Dec. 1974.

Primary Examiner—Paul A. Sacher
Attorney, Agent, or Firm—Craig & Antonelli

[57]  ABSTRACT

A perimetric eye examination device is provided having light-emitting diodes for the respective light sources which are perceived during the eye examinations. These light-emitting diodes are controllable for their brightness, either in linear dependence on the current, or in linear dependence on the pulse width repetition ratio of current pulses supplied to the light-emitting diode. The brightness perceived from the respective light-emitting diodes on the surface of the perimetric eye examination device also may be varied in accordance with physiological characteristics of the eye wherein the light-emitting diodes are distributed on the surface of the device with the brightness increasing from the central area of the observation area toward the periphery of the observation area.

9 Claims, 7 Drawing Figures

PERIMETRIC EYE TESTING DEVICE

The present invention relates to a perimetric eye examination device of the type having a viewing area, preferably in the form of a hemispherical inner surface, with a fixation point and a number of light sources of small surface area disposed in the viewing area, in which the light sources may be of a specified type wherein the brightness of the light source or groups of light sources can be accurately controlled.

Perimetric eye testing devices having a hemispherical inner surface with groups of light sources have been described, such as in German patents No. 1,202,024 and No. 1,229,753, as well as U.S. Pat. No. 3,025,755. In these previous devices, however, incandescent lamps or neon lamps serve for the light sources. Although incandescent lamps can be varied with regard to their luminous intensity by voltage changes, the color composition thereof is also varied, i.e. the color temperature of the emitted light is changed. Furthermore, the characteristics of an incandescent lamp is changed with its burning period. Consequently, it is impossible to render the luminous density or luminosity, which designates the brightness of a light source, such as an incandescent lamp, adjustable in a simple manner by linearly varying the electric power supplied thereto, and include a constant characteristic over a long period of time.

Neon lamps, on the other hand, are basically uncontrollable in their luminous density because of their physical mode of operation.

It is an object of the present invention to provide a perimetric eye testing device wherein the light sources can be adjusted with respect to the luminous density or brightness in a simple manner with a characteristic that is constant over a long time period. This object is attained in accordance with the present invention by utilizing light-emitting diodes for the light sources.

The luminous density or brightness of light-emitting diodes are linearly dependent on the current supplied, thereby being controllable in a simple manner. Moreover, during a variation of a luminous density by a variation of the current supplied to the light-emitting diodes, the color temperature remains practically constant at least within a given range. This characteristic remains constant even after a long operating time of the light-emitting diodes.

Accordingly, the eye examination device of this invention, equipped with light-emitting diodes, permits a control of the luminous density or brightness of each light source in a technically simple manner by controlling the electric current supplied to the light-emitting diodes. It is possible, for example, to provide a simple adjustable electric resistor in series with the light-emitting diodes to control the brightness of the light-emitting diodes. Complex control circuits for maintaining the brightness at a constant value which are required with the use of incandescent lamps, such as in the previously known devices, are no longer necessary.

A further object of the present invention involves the adjusting of the brightness of the light-emitting diodes according to their distribution over the viewing area in the eye examination device. This variation of the brightness of the light-emitting diodes according to their distribution can be carried out independently of the variability of the brightness of individual light sources during the course of a series of examination. Moreover, this distribution of brightness of the light-emitting diode sources over the observation area is carried out in accordance with the physiological characteristics of the human eye wherein an observer perceives light sources centrally in the field of vision at a greater brightness than toward the periphery of the field of vision. In particular, the light sensitivity of the human eye decreases from the center toward the periphery of the field of vision such that light sources closer to the center are more readily recognizable even when compared to equally bright light sources along the periphery.

Accordingly, the present invention achieves this object by providing the light-emitting diode sources in a distribution wherein the brightness increases from the center of the observation area toward the outside in correspondence with the light sensitivity characteristics of the human eye. In this manner, light sources at the periphery of the observation area are as recognizable by the eye as those close to the center so that examinations may render the physiological factors inoperative.

Another object of the present invention is the utilization of a single light-emitting diode as the fixation point for the eye to be tested.

The present invention further contemplates the ability to execute certain color vision examinations within the scope of the perimetric examination which can be carried out with the device of this invention. For example, several light-emitting diodes can emit light of different colors. In this connection, it is also possible to provide light-emitting diodes which respectively emit light of different colors, or light-emitting diodes which individually can vary the color emitted by means of an appropriate electric control, such as by variation of the current within certain limits of the characteristics of the light-emitting diodes. In this respect, there can be utilized multiple layer light-emitting diodes in which the different layers emit light of different colors in accordance with the supply of current to the different layers.

A still further object of the present invention exists in the utilization of current pulses supplied to the light-emitting diodes in order to control the luminous density or brightness. This object is achieved through the characteristics of light-emitting diodes in that the response time is extremely short so that flash-like representations of the light sources can be effected with preciseness. In this aspect of the present invention, rectangular current pulses can be applied to the light-emitting diodes at uniform amplitude and with a pulse repetition frequency greater than the flicker frequency, i. e. the frequency at which the human eye no longer recognizes successive pulses, but perceives a continuous impression of light, corresponding to the chronological median value of the light pulses.

This aspect of the present invention is important, especially when utilizing the light-emitting diodes in the portions of their characteristic curves wherein a non-linear dependency occurs between the luminous density and the current. This especially occurs at the end regions of the luminosity verses current curves, and involves changes in the color hues. Such non-linear dependency results in difficulties in the setting of predetermined luminous density values for examinations which are to be qualitativity repeated and compared with one another. Furthermore, changes in the color hue leads to an undesirable shift of the measurement into a corresponding color vision field.

Consequently, this object of the present invention provides an electronically simple adjustment of light-emitting diodes used for the light sources of a perimetric eye examination device, in which the physiological brightness impression emanating from the light-emitting diode can be adjusted linearly dependent upon electrical values which may be varied without difficulty. For example, the brightness perception of the light-emitting diodes is controlled by the application of the current pulses of uniform amplitude and at a pulse repetition frequency above the flicker frequency, as indicated above, by varying the pulse width repetition ratio, i.e. the pulse width to the time period in which the pulse is repeated. The pulses of current supplied to the light-emitting diode can be produced by an electronic pulse generator, which is controlled with respect to the pulse width and/or frequency.

This aspect of the present invention is derived from the fact that perception of the brightness of light may be varied by a corresponding variation of the pulsing control even though the amplitude of the current supplied to the diode, and consequently the luminous color of the light emitted by the diode, remain unchanged. This occurs when the frequency of the pulses is greater than the flicker frequency, about 50 hertz since the brightness impression sensed by the eye is linearly dependent on the pulse width repetition ratio, i.e. the ratio of the pulse width to the pulse repetition time in the pulse sequence of the supply current. Thus, the technical possibility is afforded of producing pulse widths of 1 microsecond with a sufficiently ideal rectangular shape, which permits a change in the brightness impression strictly proportional to the pulse width repetition ratio of the supply current, such as in a ratio of 1 to $5 \times 10^4$ without the occurrence of color changes.

These and other aspects of the present invention may be further understood by reference to the drawing figures, which illustrate in non-limitative embodiments the features of the present invention, wherein FIG. 1 shows a perspective view of the perimetric eye-testing device in which the present invention is utilized;

Figure 1:
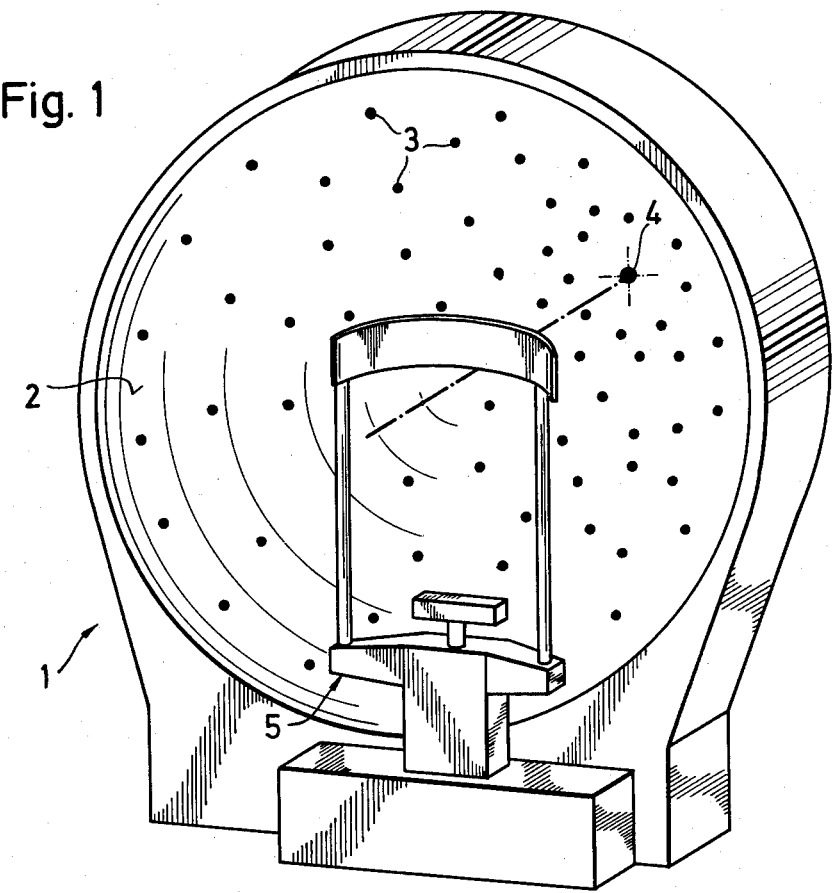

In detail, FIG. 1 illustrates a perimetric eye-testing device 1 in which a plurality of light-emitting diodes 3 is arranged in the hemispherical observation area 2 in accordance with the principles of the present invention. The perimetric eye-testing device 1 is provided with a headrest 5 located in front of the observation area 2. A fixation point 4 is located in front of the headrest 5 such that an observer, or person whose eyes are to be examined, can maintain his head in the headrest 5 and his eyes fixed on the fixation point 4 during the examination. In accordance with the principles of the present invention, the fixation point 4 may be constituted by a light-emitting diode.

Figure 2:
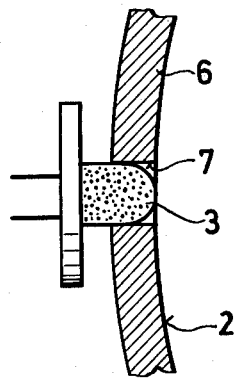
FIG. 2 shows a light-emitting diode appearing in the observation area of the device of FIG. 1 on an enlarged scale.

The light-emitting diodes 3 may be inserted into apertures 7 of the hemispherical shell 6, the inner surface of which forms the observation area 2. Thus, for example, the light-emitting diode 3 is illustrated in FIG. 2 as projecting into the aperture 7 to provide a light source surface at the inner side of the hemispherical shell 6. A plurality of these light-emitting diodes are distributed throughout the surface of the hemispherical shell 6 to constitute the observation area 2 useful for the perimetric examinations.

Figure 3:
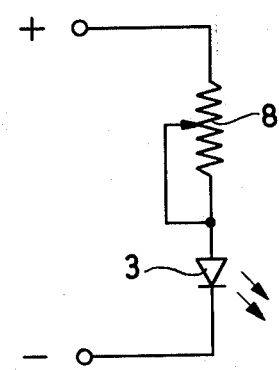
FIG. 3 shows a simple electrical circuit for controlling the luminous density of a light-emitting diode in accordance with the principles of the present invention.

Each of the light-emitting diodes 3 may be controlled in a simple manner, such as with the use of a potentiometer circuit 8, as illustrated in FIG. 3. This control of the electric current supplied to the light-emitting diode 3 provides a control of the luminous density or brightness of the diode 3 in linear dependence of the current.

This control of the brightness of the diode 3 may be effected on an individual basis in accordance with the potentiometer 8 in FIG. 3 for each of the respective diodes located on the surface of the observation area 2. Furthermore, the distribution of the light-emitting diodes 3 in the observation area 2 from the fixation point 4 outwardly towards the periphery of the observation area may be made in such a manner that the brightness of the respective diodes is increased from the fixation point 4, or central area of the observation area, toward the outer periphery of the observation area. By this means, the physiological characteristic of the human eye in discerning light sources directly ahead, or centrally located in the observation area, better than those along the periphery of the observation area, or field of view, may be compensated.

In addition, color vision examinations can be carried out within the scope of the perimeter according to the present invention by the use of several light-emitting diodes that emit different colored light. This difference in the color emitted may be achieved by the use of different light-emitting diodes, by variation of the current within certain limits of similar light-emitting diodes, and/or by the use of multi-layer light-emitting diodes which emit light of differing colors according to the supplying of electric current to the different layers.

Figure 4:
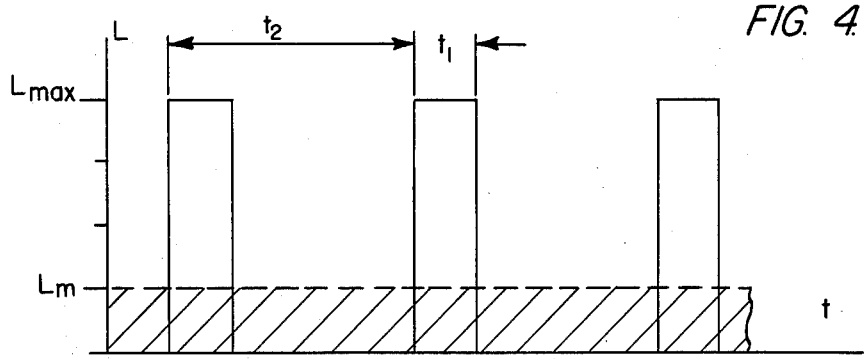
FIG. 4 shows a diagram useful in the understanding of the present invention wherein a number of light pulses are illustrated in dependence on the time.
Figure 6:
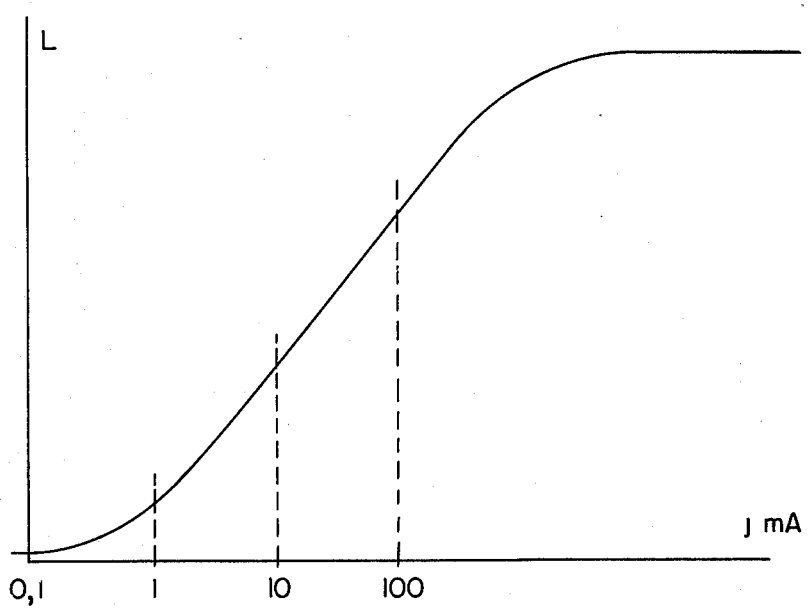
FIG. 6 is a diagram showing the luminous density or brightness of a light-emitting diode in dependence on the current.
Figure 7:
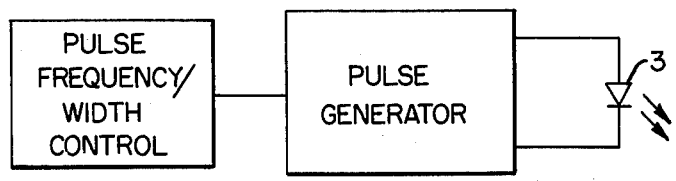
FIG. 7 shows a circuit diagram useful in supplying current pulses to a light-emitting diode.

As a further means of controlling the brightness impression of the light-emitting diodes used as the light sources in perimetric eye examinations, particularly in the non-linear regions of the characteristics of the diodes, as illustrated in FIG. 6, the current supplied to the diode may be in the form of current pulses. In this respect, as illustrated in FIG. 4, the luminous density L or brightness of a light-emitting diode occurs as a pulse in accordance with the current pulses. As may be seen in FIG. 4, a number of luminous pulses of the same height occur with a pulse sequence, or period, of $t_2$ in accordance with corresponding current pulses of uniform amplitude. The time $t_2$ is shorter than the reciprocal value of the flicker frequency limit, i.e. the frequency at which the human eye can no longer perceive the pulses in an oscillation process. The individual luminous pulses thereby result in an average physiologically effective brightness impression $L_m$ of a constant value.

Figure 5:
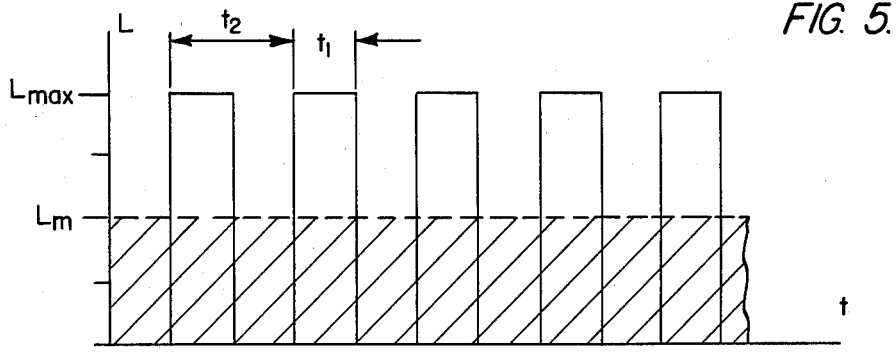
FIG. 5 shows a similar diagram of FIG. 4, but with a different pulse sequence and pulse width repetition ratio.

From FIG. 5, it can be seen that for the same amplitude luminous pulse, but with a smaller repetition time $t_2'$, such as only half as long, the physiologically effective average brightness impression $L_m$ is greater than that of FIG. 4, even though the same amplitude current pulses are utilized. In this instance, where the time $t_2'$ is only half as long as $t_2$, the effective average brightness impression $L_m$ has increased to twice as great as that in FIG. 4. Consequently, it may be seen that the brightness impression $L_m$ perceived by an observer's eye is controlled by controlling the pulse width repetition ratio, i.e. the value of $t_1$ to $t_2$, as long as the frequency of the pulses is greater than the flicker frequency even though the current amplitude is maintained constant.

This aspect of the present invention can be achieved in a simple electronic circuit, such as by the provision of a conventional pulse generator which is controllable with respect to the pulse width and/or frequency.

The brightness impression sensed by the eye is linearly dependent on the pulse width repetition ratio regardless of the dependency of the luminous density L of a light-emitting diode on the current flowing therethrough, as illustrated in FIG. 6. Therefore, even where the luminous density of a diode does not depend on the current in a linear manner, the average brightness impression which is perceived by the observer may be varied linearly by controlling the pulse width repetition ratio.

While we have shown and described several embodiments in accordance with the present invention, it is understood that the same is not limited thereto but is susceptible of numerous changes and modifications as known to those skilled in the art, and we therefore do not wish to be limited to the details shown and described herein but intend to cover all such changes and modifications as are encompassed by the scope of the appended claims.

What is claimed is:

1. In a perimetric eye examination device including a viewing area in the form of a hemispherical inner surface, a plurality of light sources of small surface area disposed in said surface, and capable of being activated in groups or individually, and a fixation point in said surface, the improvement comprising each of said light sources including light-emitting diodes, and luminous density control means for changing the brightness impression of the light-emitting diodes, said control means comprising current pulse means for supplying current pulses of uniform amplitude and at a pulse repetition frequency greater than the flicker frequency to each of said light-emitting diodes, and means for varying the pulse width repetition ratio of said current pulses supplied to said light-emitting diodes.

2. A perimetric eye examination device according to claim 1, wherein said light-emitting diodes are distributed over the viewing area of said inner surface, and the luminous density of said light-emitting diodes increases from the center of the viewing area toward the periphery thereof.

3. A perimetric eye examination device according to claim 1, wherein said fixation point is constituted by one of said light-emitting diodes.

4. A perimetric eye examination device according to claim 1, wherein said light-emitting diodes emit light of different colors.

5. A perimetric eye examination device according to claim 4, wherein means for electrically controlling each of said light-emitting diodes is provided for varying the color of the light emitted by the respective diode.

6. A perimetric eye examination device according to claim 1, wherein said current pulses have a rectangular configuration.

7. A perimetric eye examination device according to claim 6, wherein said current pulse means and said means for varying the pulse width repetition ratio include a pulse generator and a pulse width control circuit respectively.

8. A perimetric eye examination device according to claim 1, wherein said current pulse means and said means for varying the pulse width repetition ratio include a pulse generator and a pulse frequency control circuit, respectively.

9. A perimetric eye examination device according to claim 1, wherein said luminous density control means effects linear brightness impression by the eye independently of the luminous density-current relationship of said light-emitting diodes so as to operate said light-emitting diodes in non-linear regions of the luminous density-current relationship of said light-emitting diodes.

* * * * *